(12) United States Patent
Yoshida

(10) Patent No.: US 6,907,393 B1
(45) Date of Patent: Jun. 14, 2005

(54) METHODS FOR SCREENING CANDIDATES FOR ARTIFICIAL PROMOTORS

(75) Inventor: Tetsuhiko Yoshida, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 450 days.

(21) Appl. No.: 10/110,242

(22) PCT Filed: Oct. 12, 2000

(86) PCT No.: PCT/JP00/07105

§ 371 (c)(1),
(2), (4) Date: May 7, 2002

(87) PCT Pub. No.: WO01/27259

PCT Pub. Date: Apr. 19, 2001

(30) Foreign Application Priority Data

Oct. 13, 1999 (JP) .......................................... 11-291295

(51) Int. Cl.⁷ .......................... G06G 7/60; G06F 19/00; G05B 15/00; G11C 17/00
(52) U.S. Cl. .............................. 703/11; 702/20; 700/1; 365/94
(58) Field of Search ............................. 703/11; 702/20; 700/1; 365/94

(56) References Cited

PUBLICATIONS

Tomii et al., "Analysis of Amino Acid Indices and Mutation Matrices for Sequence Comparison and Structure Prediction of Proteins," *Protein Engineering*, vol. 9, No. 1, pp 27–36 (1996).

Kawashima et al., "Aaindex: Amino Acid Index Database," *Nucleic Acids Research*, vol. 27, No. 1, pp 368–369 (Jan. 1, 1999).

Von Heijne et al., "Trans–membrane Translocation of Proteins: The Direct Transfer Model," *European Journal of Biochemistry*, vol. 97, No. 1, pp 175–181 (1979).

Fickett et al., "Eukaryotic Promoter Recognition," *Genome Research*, vol. 7 No. 9, pp 861–878 (Sep. 1997).

Pedersen et al., "The Biology of Eukaryotic Promoter Prediction–a Review," *Computers & Chemistry*, vol. 23, No. 3–4, pp 191–207 (Jun. 15, 1999).

Qing K. Chen et al., "PromFD 1.0: a computer program that predicts eukaryotic pol II promoters using strings and IMD matrices", CABIOS 1997, vol. 13, No. 1, pp. 29–35.

Petra Sazelova et al., "In vitro and in vivo transcription from a computer predicted promoter", 1997, vol. 187, No. 2, pp. 281–287.

*Primary Examiner*—John S. Brusca
(74) *Attorney, Agent, or Firm*—Oliff & Berridge, PLC

(57) ABSTRACT

The present invention provides methods for selecting artificial promotor candidates that reduce the number of promotors required to be evaluated by actual experimentation when designing artificial promotor candidates that are potentially effective for structural genes. In these artificial promotor candidate selection methods, a randomly selected nucleotide sequence is joined upstream of a structural gene (S1). Next, nucleotides are extracted in a predetermined pattern from a designated region containing at least the transcription start site of the joined nucleotide sequence, thereby generating a virtual amino acid sequence, and an index curve is generated from the virtual amino acid sequence (S2, S3). Then, the nucleotide sequence joined upstream of the structural gene is selected as an artificial promotor candidate if the index curve exhibits a sign change near the transcription start site (S4).

8 Claims, 16 Drawing Sheets

FIG. 1
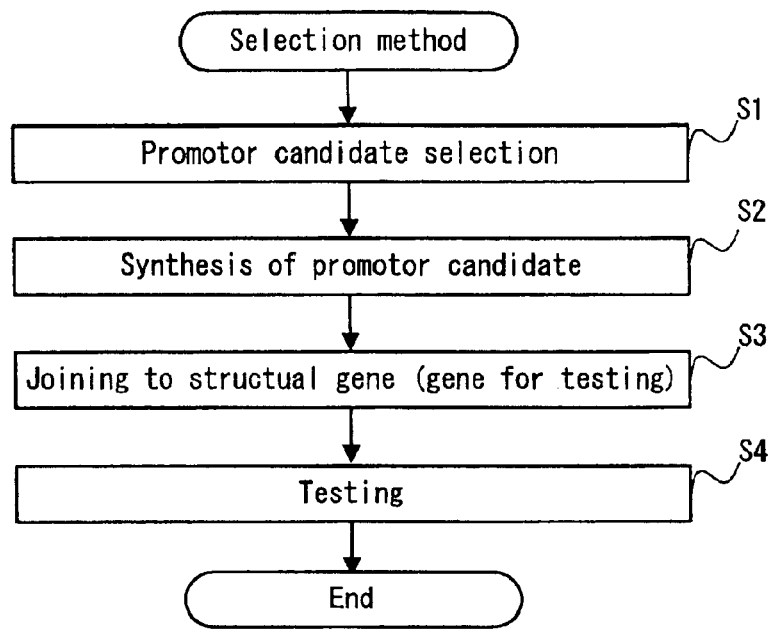
Method of the present Invention
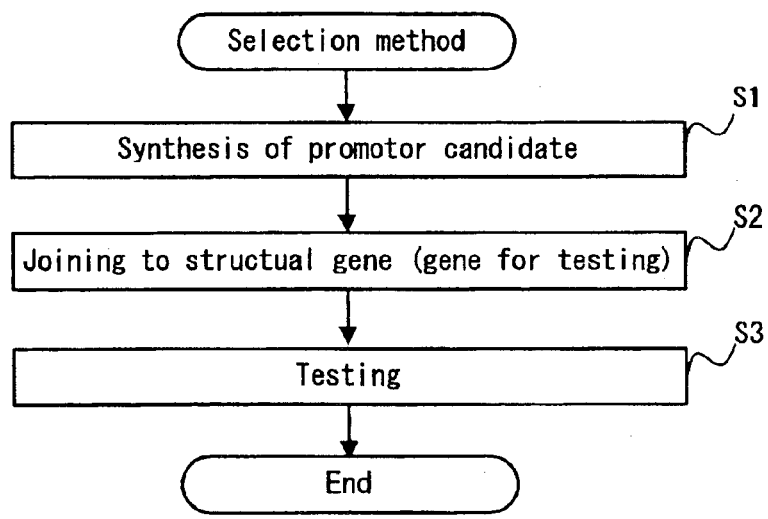
Prior-art Method

FIG. 3

Nucleotide sequence(example)
g a t c t c c t c · · c a / c c c g t c c a g · ·
Promotor                  Structural gene (1) Pattern 1
- Nucleotide sequence g a t c t c c t c g g c g a a c a · ·
g a t      → D → 23.22
   a t c      → I → -18.32
     t c t      → S → -1.54
       c t c      → L → -17.79
         t c c      → S → -1.54

(2) Pattern 2
- Nucleotide sequence g a t c t c c t c g g c g a a c a · ·
g * t * t      → V → -16.22
   a * c * c      → T → -4.15
     t * t * c      → F → -21.98

(3) Pattern 3
- Nucleotide sequence g a t c t c c t c g g c g a a c a · ·
g * * c * * c      → A → -12.04
   a * * t * * t      → I → -18.32
     t * * c * * c      → S → -1.54

FIG. 4

| First nucleotide | | Second nucleotide | | | | | | | | Third nucleotide |
|---|---|---|---|---|---|---|---|---|---|---|
| | | t | | c | | a | | g | | |
| | t | ttt<br>ttc | F | tct<br>tcc | S | tat<br>tac | Y | tgt<br>tgc | C | t<br>c |
| | | tta<br>ttg | L | tca<br>tcg | | taa<br>tag | stop | tga<br>tgg | stop<br>W | a<br>g |
| | c | ctt<br>ctc | L | cct<br>ccc | P | cat<br>cac | H | cgt<br>cgc | R | t<br>c |
| | | cta<br>ctg | | cca<br>ccg | | caa<br>cag | Q | cga<br>cgg | | a<br>g |
| | a | att<br>atc | I | act<br>acc | T | aat<br>aac | N | agt<br>agc | S | t<br>c |
| | | ata | | aca | | aaa<br>aag | K | aga<br>agg | R | a |
| | | atg | M | acg | | | | | | g |
| | g | gtt<br>gtc | V | gct<br>gcc | A | gat<br>gac | D | ggt<br>ggc | G | t<br>c |
| | | gta<br>gtg | | gca<br>gcg | | gaa<br>gag | E | gga<br>ggg | | a<br>g |

FIG. 5

| Example letter code for amino acid | Amino acid index value |
|---|---|
| A (alanine) | −12.04 |
| R (arginine) | 39.23 |
| N (aspragine) | 4.25 |
| D (aspartic acid) | 23.22 |
| C (cysteine) | 3.95 |
| Q (glutamine) | 2.16 |
| E (glutamic acid) | 16.81 |
| G (glycine) | −7.85 |
| H (histidine) | 6.28 |
| I (isoleucine) | −18.32 |
| L (leucine) | −17.79 |
| K (lysine) | 9.71 |
| M (methionine) | −8.86 |
| F (phenylalanine) | -21.98 |
| P (proline) | 5.82 |
| S (serine) | −1.54 |
| T (threonine) | −4.15 |
| W (tryptophan) | −16.19 |
| Y (tyrosine) | −1.51 |
| V (valine) | −16.22 |
| X (STOP) *1 | 0.00 |

· transfer free energy to lipophilic phase, von Heijne-Blomberg 1979

*1 : Represents a codon that calls for an end of protein synthesis (end of translation)

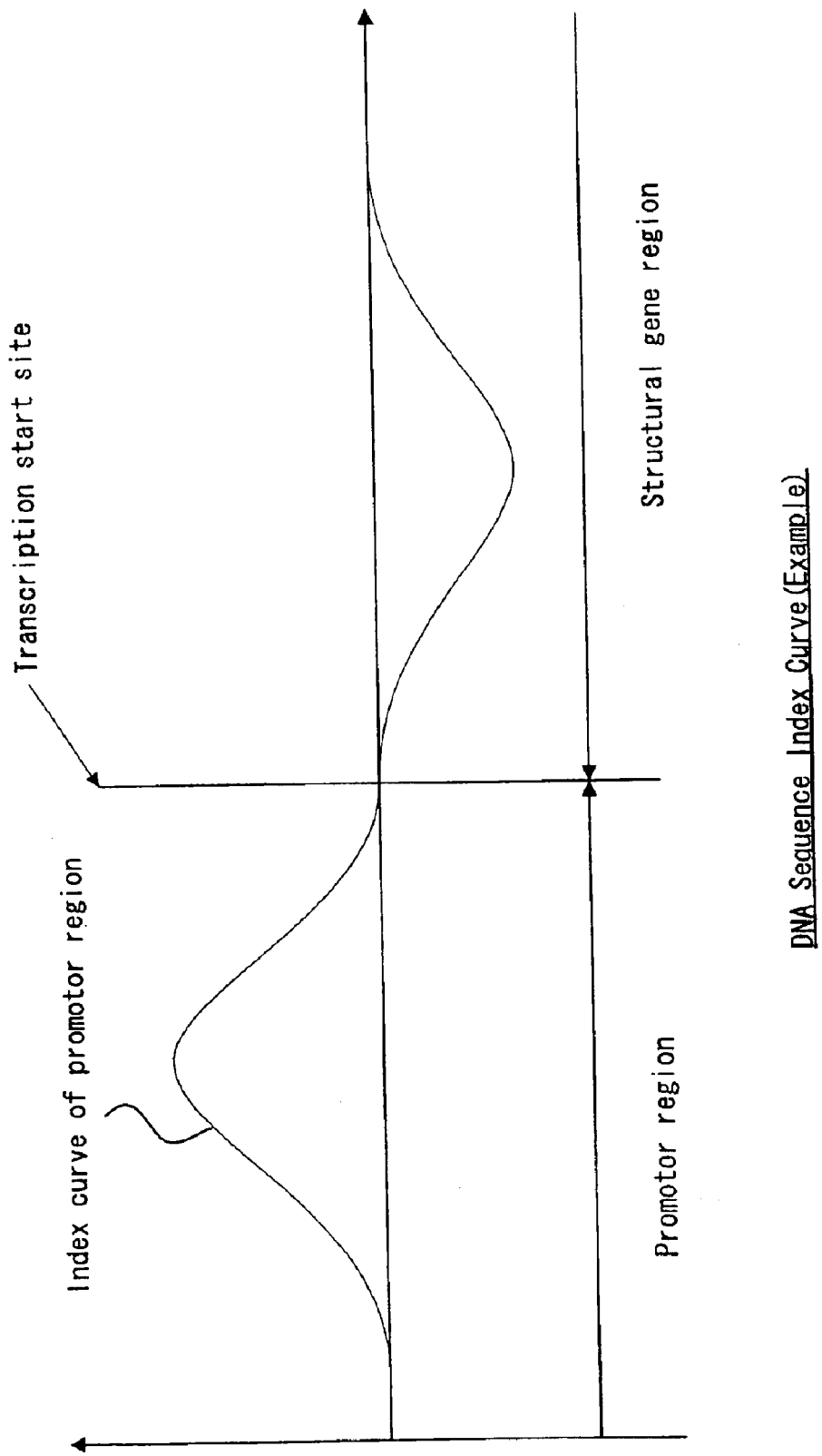

FIG.7

```
  1 ccggattagcagagcgatgatggcacaaacggtgctacagagttcttgaagtagtggccc
 61 gactacggctacactagaaggacagtatttggtatctgcgctctgctgaagccagttacc
121 ttcggaaaaagagttggtagctcttgatccgg
```

FIG.8

```
  1 gatctcctcggcgaacacacccgtccagctcggcttggacgggctgccgatctcacggga
 61 gagctcggtcgtggcgtcgaggtgggcragtgtgccggcgccgggtcggtgtagtcgtcc
121 gcggggacgtagatcgcgtcggtttccgtgtccgcacgggagaatccattgtctgcatta
181 ccgctgtgtaacgttttkcgagcctcgttttgcattcattgccgacggtacctgagggtc
241 agtcttatcccgcgccggaccaggcactctcgcacgcccgtgcsgcgcgcaacacttcgc
301 acaggaggaacattgcacatcaagggaagaaaggtcgggctcgcggtcagcgccgtcgcc
361 ggtgtcgcsctctcgctctgtcagcctgcaccacgtccggcaccggtggttcgtccgctg
421 ctaaaggggcatggtgacagtggcggtcgtcaacgacctcacctcactgaactcgcaga
481 ccccgcagggcaacctggacaccaacggccaggtcggctacctgaagttcctacggaacc
541 ggtttccagtacatcgacaacaactacaa
```

FIG.9

```
  1 gagaacacagctggaattttttacaaaggtagttggtgaagctagtcagcgaatcccatt
 61 accttccactctacctaaccccttcaccaacaacaaatttctgtaatttaaaaactagc
121 caaaaagaactctcttttacaaagagccaaagactcaatctttactttcaagaa
```

FIG.10

```
  1 tcaattgctacaatcacttcattattaattttaattaatatatgtggttatatatgaaac
 61 tgttagagaaataatagctccaccatattttttctcaatttattttcactataaaaagg
121 ctatttcattataatcaaaacaagacacacacaaagagaaggagcaataaaataaaagta
181 aacaacaatttgtgtgtttaaaaaaaaaaaaaaagtacacacaccaaaaaaaaaaattc
```

FIG.11

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| c | c | g | g | a | t | t | a | g | c | a | g | a | g | c |
| 16 | 17 | 18 | 19 | 20 | 21 | 22 | 23 | 24 | 25 | 26 | 27 | 28 | 29 | 30 |
| g | a | t | g | a | t | g | g | c | a | c | a | a | a | c |
| 31 | 32 | 33 | 34 | 35 | 36 | 37 | 38 | 39 | 40 | 41 | 42 | 43 | 44 | 45 |
| g | g | t | g | c | t | a | c | a | g | a | g | t | t | c |
| 46 | 47 | 48 | 49 | 50 | 51 | 52 | 53 | 54 | 55 | 56 | 57 | 58 | 59 | 60 |
| t | t | g | a | a | g | t | a | g | t | g | g | c | c | c |
| 61 | 62 | 63 | 64 | 65 | 66 | 67 | 68 | 69 | 70 | 71 | 72 | 73 | 74 | 75 |
| g | a | c | t | a | c | g | g | c | t | a | c | a | c | t |
| 76 | 77 | 78 | 79 | 80 | 81 | 82 | 83 | 84 | 85 | 86 | 87 | 88 | 89 | 90 |
| a | g | a | a | g | g | a | c | a | g | t | a | t | t | t |
| 91 | 92 | 93 | 94 | 95 | 96 | 97 | 98 | 99 | 100 | 101 | 102 | 103 | 104 | 105 |
| g | g | t | a | t | c | t | g | c | g | c | t | c | t | g |
| 106 | 107 | 108 | 109 | 110 | 111 | 112 | 113 | 114 | 115 | 116 | 117 | 118 | 119 | 120 |
| c | t | g | a | a | g | c | c | a | g | t | t | a | c | c |
| 121 | 122 | 123 | 124 | 125 | 126 | 127 | 128 | 129 | 130 | 131 | 132 | 133 | 134 | 135 |
| t | t | c | g | g | a | a | a | a | a | g | a | g | t | t |
| 136 | 137 | 138 | 139 | 140 | 141 | 142 | 143 | 144 | 145 | 146 | 147 | 148 | 149 | 150 |
| g | g | t | a | g | c | t | c | t | t | g | a | t | c | c |
| 151 | 152 | | | | | | | | | | | | | |
| g | g | | | | | | | | | | | | | |

FIG.12

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| ccg | cgg | gga | gat | att | tta | tag | agc | gca | cag | aga | gag | agc | gcg | cga |
| 16 | 17 | 18 | 19 | 20 | 21 | 22 | 23 | 24 | 25 | 26 | 27 | 28 | 29 | 30 |
| gat | atg | tga | gat | atg | tgg | ggc | gca | cac | aca | caa | aaa | aac | acg | cgg |
| 31 | 32 | 33 | 34 | 35 | 36 | 37 | 38 | 39 | 40 | 41 | 42 | 43 | 44 | 45 |
| ggt | gtg | tgc | gct | cta | tac | aca | cag | aga | gag | agt | gtt | ttc | tct | ctt |
| 46 | 47 | 48 | 49 | 50 | 51 | 52 | 53 | 54 | 55 | 56 | 57 | 58 | 59 | 60 |
| ttg | tga | gaa | aag | agt | gta | tag | agt | gtg | tgg | ggc | gcc | ccc | ccg | cga |
| 61 | 62 | 63 | 64 | 65 | 66 | 67 | 68 | 69 | 70 | 71 | 72 | 73 | 74 | 75 |
| gac | act | cta | tac | acg | cgg | ggc | gct | cta | tac | aca | cac | act | cta | tag |
| 76 | 77 | 78 | 79 | 80 | 81 | 82 | 83 | 84 | 85 | 86 | 87 | 88 | 89 | 90 |
| aga | gaa | aag | agg | gga | gac | aca | cag | agt | gta | tat | att | ttt | ttg | tgg |
| 91 | 92 | 93 | 94 | 95 | 96 | 97 | 98 | 99 | 100 | 101 | 102 | 103 | 104 | 105 |
| ggt | gta | tat | atc | tct | ctg | tgc | gcg | cgc | gct | ctc | tct | ctg | tgc | gct |
| 106 | 107 | 108 | 109 | 110 | 111 | 112 | 113 | 114 | 115 | 116 | 117 | 118 | 119 | 120 |
| ctg | tga | gaa | aag | agc | gcc | cca | cag | agt | gtt | tta | tac | acc | cct | ctt |
| 121 | 122 | 123 | 124 | 125 | 126 | 127 | 128 | 129 | 130 | 131 | 132 | 133 | 134 | 135 |
| ttc | tcg | cgg | gga | gaa | aaa | aaa | aaa | aag | aga | gag | agt | gtt | ttg | tgg |
| 136 | 137 | 138 | 139 | 140 | 141 | 142 | 143 | 144 | 145 | 146 | 147 | 148 | 149 | 150 |
| ggt | gta | tag | agc | gct | ctc | tct | ctt | ttg | tga | gat | atc | tcc | ccg | cgg |
| 151 | 152 | 153 | | | | | | | | | | | | |
| gg | g | | | | | | | | | | | | | |

FIG.13

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| 5.8 | 39.2 | -7.9 | 23.2 | -18.3 | -17.8 | 0.0 | -1.5 | -12.0 | 2.2 | 39.2 | 16.8 | -1.5 | -12.0 | 39.2 |
| 16 | 17 | 18 | 19 | 20 | 21 | 22 | 23 | 24 | 25 | 26 | 27 | 28 | 29 | 30 |
| 23.2 | -8.9 | 0.0 | 23.2 | -8.9 | -16.2 | -7.9 | -12.0 | 6.3 | -4.2 | 2.2 | 9.7 | 4.3 | -4.2 | 39.2 |
| 31 | 32 | 33 | 34 | 35 | 36 | 37 | 38 | 39 | 40 | 41 | 42 | 43 | 44 | 45 |
| -7.9 | -16.2 | 4.0 | -12.0 | -17.8 | -1.5 | -4.2 | 2.2 | 39.2 | 16.8 | -1.5 | -16.2 | -22.0 | -1.5 | -17.8 |
| 46 | 47 | 48 | 49 | 50 | 51 | 52 | 53 | 54 | 55 | 56 | 57 | 58 | 59 | 60 |
| -17.8 | 0.0 | 16.8 | 9.7 | -1.5 | -16.2 | 0.0 | -1.5 | -16.2 | -16.2 | -7.9 | -12.0 | 5.8 | 5.8 | 39.2 |
| 61 | 62 | 63 | 64 | 65 | 66 | 67 | 68 | 69 | 70 | 71 | 72 | 73 | 74 | 75 |
| 23.2 | -4.2 | -17.8 | -1.5 | -4.2 | 39.2 | -7.9 | -12.0 | -17.8 | -1.5 | -4.2 | 6.3 | -4.2 | -17.8 | 0.0 |
| 76 | 77 | 78 | 79 | 80 | 81 | 82 | 83 | 84 | 85 | 86 | 87 | 88 | 89 | 90 |
| 39.2 | 16.8 | 9.7 | 39.2 | -7.9 | 23.2 | -4.2 | 2.2 | -1.5 | -16.2 | -1.5 | -18.3 | -22.0 | -17.8 | -16.2 |
| 91 | 92 | 93 | 94 | 95 | 96 | 97 | 98 | 99 | 100 | 101 | 102 | 103 | 104 | 105 |
| -7.9 | -16.2 | -1.5 | -18.3 | -1.5 | -17.8 | 4.0 | -12.0 | 39.2 | -12.0 | -17.8 | -1.5 | -17.8 | 4.0 | -12.0 |
| 106 | 107 | 108 | 109 | 110 | 111 | 112 | 113 | 114 | 115 | 116 | 117 | 118 | 119 | 120 |
| -17.8 | 0.0 | 16.8 | 9.7 | -1.5 | -12.0 | 5.8 | 2.2 | -1.5 | -16.2 | -17.8 | -1.5 | -4.2 | 5.8 | -17.8 |
| 121 | 122 | 123 | 124 | 125 | 126 | 127 | 128 | 129 | 130 | 131 | 132 | 133 | 134 | 135 |
| -22.0 | -1.5 | 39.2 | -7.9 | 16.8 | 9.7 | 9.7 | 9.7 | 9.7 | 39.2 | 16.8 | -1.5 | -16.2 | -17.8 | -16.2 |
| 136 | 137 | 138 | 139 | 140 | 141 | 142 | 143 | 144 | 145 | 146 | 147 | 148 | 149 | 150 |
| -7.9 | -16.2 | 0.0 | -1.5 | -12.0 | -17.8 | -1.5 | -17.8 | -17.8 | 0.0 | 23.2 | -18.3 | -1.5 | 5.8 | 39.2 |
| 151 | 152 | 153 | 154 | 155 | | | | | | | | | | |
| 0.0 | 0.0 | 0.0 | 0.0 | 0.0 | | | | | | | | | | |

FIG.14

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
|   |   |   |   |   | 24.3 | 18.5 | -22.3 | -26.5 | -47.5 | 10.0 | 44.6 | 43.1 | 32.6 | 83.9 |
| 16 | 17 | 18 | 19 | 20 | 21 | 22 | 23 | 24 | 25 | 26 | 27 | 28 | 29 | 30 |
| 104.9 | 56.8 | 40.0 | 64.8 | 68.0 | 12.5 | -18.5 | -21.7 | -15.4 | -42.8 | -31.8 | -5.9 | 6.2 | 14.1 | 47.1 |
| 31 | 32 | 33 | 34 | 35 | 36 | 37 | 38 | 39 | 40 | 41 | 42 | 43 | 44 | 45 |
| 43.4 | 25.0 | 19.2 | 2.9 | -10.7 | -51.5 | -47.8 | -29.4 | 5.9 | 34.8 | 51.0 | 36.3 | 18.5 | 14.8 | -42.3 |
| 46 | 47 | 48 | 49 | 50 | 51 | 52 | 53 | 54 | 55 | 56 | 57 | 58 | 59 | 60 |
| -76.9 | -75.3 | -42.3 | -10.6 | -10.6 | -9.0 | 8.8 | 7.2 | -25.8 | -51.7 | -58.0 | -53.8 | -48.0 | -40.7 | 14.8 |
| 61 | 62 | 63 | 64 | 65 | 66 | 67 | 68 | 69 | 70 | 71 | 72 | 73 | 74 | 75 |
| 54.2 | 57.9 | 52.2 | 44.8 | 34.9 | 34.9 | 3.8 | -4.1 | -4.1 | -4.1 | -4.1 | -37.1 | -33.4 | -39.1 | -21.3 |
| 76 | 77 | 78 | 79 | 80 | 81 | 82 | 83 | 84 | 85 | 86 | 87 | 88 | 89 | 90 |
| 19.4 | 40.4 | 43.8 | 87.2 | 97.1 | 120.4 | 77.0 | 62.3 | 51.1 | -4.4 | 2.0 | -39.6 | -57.4 | -77.4 | -92.0 |
| 91 | 92 | 93 | 94 | 95 | 96 | 97 | 98 | 99 | 100 | 101 | 102 | 103 | 104 | 105 |
| -83.6 | -98.4 | -81.5 | -77.9 | -61.6 | -63.2 | -51.4 | -47.3 | -6.5 | -0.2 | -16.5 | -0.2 | -22.0 | -6.0 | -57.3 |
| 106 | 107 | 108 | 109 | 110 | 111 | 112 | 113 | 114 | 115 | 116 | 117 | 118 | 119 | 120 |
| -63.0 | -45.2 | -26.9 | 0.7 | -4.8 | -4.8 | 18.8 | 20.9 | 2.6 | -23.4 | -39.6 | -29.1 | -39.1 | -35.4 | -51.6 |
| 121 | 122 | 123 | 124 | 125 | 126 | 127 | 128 | 129 | 130 | 131 | 132 | 133 | 134 | 135 |
| -57.4 | -41.2 | -0.4 | -4.1 | 6.9 | 34.4 | 66.1 | 77.3 | 47.8 | 94.9 | 94.9 | 83.6 | 57.7 | 30.2 | 4.3 |
| 136 | 137 | 138 | 139 | 140 | 141 | 142 | 143 | 144 | 145 | 146 | 147 | 148 | 149 | 150 |
| -42.8 | -75.8 | -74.3 | -59.6 | -53.8 | -55.4 | -49.1 | -50.7 | -68.5 | -66.9 | -31.7 | -32.2 | -32.2 | -8.6 | 48.4 |
| 151 | 152 | 153 | 154 | 155 |   |   |   |   |   |   |   |   |   |   |
| 48.4 | 25.2 | 43.5 | 45.1 | 39.3 |   |   |   |   |   |   |   |   |   |   |

SEQUENCE LISTING

<160> NUMBER OF SEQ ID NOS: 9

<210> SEQ ID NO 1
<211> LENGTH: 152
<212> TYPE: DNA
<213> ORGANISM: Plasmid Colicin E1

<400> SEQUENCE: 1

```
ccggattagc agagcgatga tggcacaaac ggtgctacag agttcttgaa gtagtggccc        60
gactacggct acactagaag gacagtattt ggtatctgcg ctctgctgaa gccagttacc       120
ttcggaaaaa gagttggtag ctcttgatcc gg                                     152
```

<210> SEQ ID NO 2
<211> LENGTH: 569
<212> TYPE: DNA
<213> ORGANISM: Clavibacter xyli

<400> SEQUENCE: 2

```
gatctcctcg gcgaacacac ccgtccagct cggcttggac gggctgccga tctcacggga        60
gagctcggtc gtggcgtcga ggtgggcrag tgtgccggcg ccgggtcggt gtagtcgtcc       120
gcggggacgt agatcgcgtc ggtttccgtg tccgcacggg agaatccatt gtctgcatta       180
ccgctgtgta acgttttkcg agcctcgttt tgcattcatt gccgacggta cctgagggtc       240
agtcttatcc cgcgccggac caggcactct cgcacgcccg tgcsgcgcgc aacacttcgc       300
acaggaggaa cattgcacat caagggaaga aaggtcgggc tcgcggtcag cgccgtcgcc       360
ggtgtcgcsc tctcgctctg tcagcctgca ccacgtccgg caccggtggt tcgtccgctg       420 ctaaagggg catggtgaca gtggcggtcg tcaacgacct cacctcactg aactcgcaga       480
```

```
ccccgcaggg caacctggac accaacggcc aggtcggcta cctgaagttc ctacggaacc    540
ggtttccagt acatcgacaa caactacaa                                      569

<210> SEQ ID NO 3
<211> LENGTH: 175
<212> TYPE: DNA
<213> ORGANISM: Petunia hybrida

<400> SEQUENCE: 3
gagaacacag ctggaatttt ttacaaaggt agttggtgaa gctagtcagc gaatcccatt    60
accttccact ctacctaacc cccttcacca acaacaaatt tctgtaattt aaaaactagc   120
caaaaaagaa ctctctttta caaagagcca aagactcaat ctttactttc aagaa        175

<210> SEQ ID NO 4
<211> LENGTH: 239
<212> TYPE: DNA
<213> ORGANISM: Lycopersicon esculentum

<400> SEQUENCE: 4
tcaattgcta caatcacttc attattaatt ttaattaata tatgtggtta tatatgaaac    60
tgttagagaa ataatagctc caccatattt ttttctcaat ttattttcac tataaaagg   120 ctatttcatt ataatcaaaa caagacacac acaaagagaa ggagcaataa aataaaagta   180
aacaacaatt tgtgtgttta aaaaaaaaaa aaaagtacac acaccaaaaa aaaaaattc    239

<210> SEQ ID NO 5
<211> LENGTH: 453
<212> TYPE: DNA
<213> ORGANISM: Artificial
<220> FEATURE:
<223> OTHER INFORMATION: Virtually-generated promotor candidate.

<400> SEQUENCE: 5
ccgcggggag atattttata gagcgcacag agagagagcg cgcgagatat gtgagatatg    60
tggggcgcac acacacaaaa aaacacgcgg ggtgtgtgcg ctctatacac acagagagag   120
agtgttttct ctcttttgtg agaaaagagt gtatagagtg tgtggggcgc ccccccgcga   180
gacactctat acacgcgggg cgctctatac acacacactc tatagagaga aaagagggga   240
gacacacaga gtgtatatat tttttgtgg ggtgtatata tctctctgtg cgcgcgcgct   300
ctctctctgt gcgctctgtg agaaaagagc gccccacaga gtgttttata cacccctctt   360
ttctcgcggg gagaaaaaaa aaaaaagaga gagagtgttt tgtggggtgt atagagcgct   420
ctctctcttt tgtgagatat ctccccgcgg ggg                                453

<210> SEQ ID NO 6
<211> LENGTH: 9
<212> TYPE: DNA
<213> ORGANISM: Artificial
<220> FEATURE:
<223> OTHER INFORMATION: Partial sequence of promotor portion of
      exemplified nucleotide sequence.

<400> SEQUENCE: 6 gatctcctc                                                             9

<210> SEQ ID NO 7
<211> LENGTH: 11
<212> TYPE: DNA
<213> ORGANISM: Artificial
```

```
<220> FEATURE:
<223> OTHER INFORMATION: Partial sequence of promotor and structural
      gene of exemplified nucleotide sequence.

<400> SEQUENCE: 7
cacccgtcca g                                                          11

<210> SEQ ID NO 8
<211> LENGTH: 5
<212> TYPE: DNA
<213> ORGANISM: Artificial
<220> FEATURE:
<223> OTHER INFORMATION: Partial sequence of promotor portion of
      exemplified nucleotide sequence.

<400> SEQUENCE: 8 gatct                                                                  5

<210> SEQ ID NO 9
<211> LENGTH: 5
<212> TYPE: PRT
<213> ORGANISM: Artificial
<220> FEATURE:
<223> OTHER INFORMATION: Virtual amino acid sequence.

<400> SEQUENCE: 9

Asp Ile Ser Leu Ser
1               5
```

METHODS FOR SCREENING CANDIDATES FOR ARTIFICIAL PROMOTORS

FIELD OF THE INVENTION

The present invention relates to artificial promotor candidate selection technology and more particularly, to artificial promotor selection technology for selecting potentially effective artificial promotor candidates from among a set of virtually-generated promotor candidates.

BACKGROUND ART

Progress in the biological sciences has enabled the analysis of the chromosomal structure at the molecular level. This analysis has determined that DNA (deoxyribonucleic acid) molecules in chromosomes are continuous, singular, thread-like strands. Four types of nucleotides, i.e., adenine (a), guanine (g), cytosine (c), and thymine (t), are present in DNA, and the DNA molecules in chromosomes are composed of combinations of these nucleotides, together with sugars and phosphoric acids that are bound thereto. The DNA molecules in chromosomes encode a variety of information by virtue of differences in nucleotide sequences.

Through the analysis of DNA, it has been determined that portions of the DNA material are structural units that carry genetic information and determine genotype, e.g., genes. The genes determine primary structure, such as proteins, tRNA, and RRNA, and are specifically defined as structural genes. The gene-based mechanism of protein synthesis will be explained with reference to FIG. 18.

As shown in FIG. 18, a gene is divided into the three regions, a promotor region, a transcription region (the structural gene region containing information relating to the amino acid sequence of the protein) and a termination region. The promotor region serves to control the start of transcription, the transcription region is the region that is actually transcribed, and the termination region controls the termination of transcription. The site where transcription begins is called the transcription start site.

Protein synthesis from genes, which are structured as described above, occurs according to the following steps. First, RNA polymerase (an enzyme that transcribes a DNA sequence) binds to a DNA sequence slightly ahead of the promotor region and then moves toward the promotor region. Once this RNA polymerase has passed the promotor region and moved to the transcription-region side of the gene, it generates messenger RNA that corresponds to the DNA sequence in the transcription region. Further, when the RNA polymerase reaches the termination region, the transcription of the DNA sequence ceases. The messenger RNA subsequently moves from the cell nucleus to the cytoplasm and binds with ribosomes. The ribosomes synthesize proteins based upon the messenger RNA. The DNA sequence of a gene is transcribed in this manner, and a specific protein is synthesized based upon this transcription.

The rate of such protein synthesis depends upon the rate at which RNA polymerase transcribes messenger RNA, and the promotor sequence of the gene controls the rate at which messenger RNA is transcribed.

Therefore, it is theoretically possible to create promotors that synthesize proteins at a high rate and promotors that synthesize proteins at a low rate by manipulating the DNA sequence of the promotor region.

In recent years, there have been many attempts to actively control the protein synthesis rate by artificially altering the DNA sequence of promotor regions. By controlling the rate of protein synthesis, it would be possible to create, e.g., promoters having a high transcription activity for use in artificially expressing specific proteins in large quantities. As a result, gene therapy would be enabled at the molecular level in which, e.g., cancer cells are infected with an adequate amount of a virus (in gene therapy, viruses of reduced toxicity are used as virus vectors to transport normal genes into cells) and proteins are then specifically expressed from these normal genes (integrated with powerful artificial promoters) in amounts that are adequate to suppress the cancer.

However, at present, a method for designing artificial promotors having high transcription activity, i.e., artificial promotors containing a DNA sequence that enable the above-noted characteristics, has not yet been established. Currently, randomly sequenced nucleotides (promotor candidates) are placed ahead of structural genes (test genes), and the efficacy of these promotor candidates is evaluated by determining whether or not the test gene is expressed.

According to this method, it is extremely difficult to identify nucleotide sequences suitable as potentially highly effective artificial promoters from a virtually infinite number of nucleotide sequences ($4^{th}$ power exponential) because the artificial promotor candidates used in the associated experimentation have randomly determined nucleotide sequences.

Therefore, it is an object of the present invention to provide artificial promotor candidate selection methods capable of reducing the number of nucleotide sequences that are actually tested by selecting, in advance of testing, nucleotide sequences that are highly likely to function as potentially effective promoters from among a set of nucleotide sequences under consideration.

DISCLOSURE OF THE INVENTION

As a result of research on the characteristics of nucleotide sequences of known promotors, virtual amino acid sequences were created by extracting amino acid information from nucleotide sequences of the promotors and structural genes using certain patterns; then, curves were generated using index values corresponding to the respective amino acids in the virtual amino acid sequences. The invention was conceived upon discovery that a sign change is very often present in the curve near the transcription start site.

According to the artificial promotor candidate selection methods of the present invention, artificial promotor candidates are selected based upon DNA nucleotide sequences, in which the corresponding virtual amino acid sequence exhibits a sign change in the amino acid index curve at a point near the transcription start site of the transcription region of the structural gene.

The artificial promotor candidate selection methods of the present invention are based upon the newly-discovered fact that a sign change usually exists near the transcription start site of a given nucleotide sequence, which contains a promotor and a structural gene, between the amino acid index curve for the promotor and the amino acid index curve for the structural gene. For example, a curve is first determined based upon on the structural gene using the amino acid index values of a virtual amino acid sequence near the transcription start site; then, a nucleotide sequence for an artificial promotor candidate can be selected such that the virtual amino acid sequence for the promotor region will be opposite in sign near the transcription start site relative to the curve of the structural gene. In addition, a pre-determined nucleotide sequence may virtually joined upstream of a structural gene, and then the efficacy of the pre-determined nucleotide sequence can be evaluated by determining whether or not the index curve of the virtual amino acid sequence, which is generated from the joined nucleotide sequence, exhibits a sign change near the transcription start site.

In another artificial promotor candidate selection method of the present invention, a candidate nucleotide sequence of an artificial promotor is virtually joined upstream of a nucleotide sequence of a structural gene; then, if the amino acid index curve of the virtual amino acid sequence, which is generated based upon the joined nucleotide sequences, exhibits a sign change near the transcription start site, the nucleotide sequence of an artificial promotor will be selected as a promotor candidate for the structural gene.

In other words, when artificial promotor candidates are being considered for selection as being potentially effective for a structural gene having a known nucleotide sequence, a candidate nucleotide sequence is joined upstream of th structural gene. If the index curve based on a virtual amino acid sequence, which is extracted in a pre-determined pattern from the joined nucleotide sequence in the region that contains at least the transcription start site of the joined nucleotide sequence, exhibits a sign change near the transcription start site, the candidate nucleotide sequence is selected as an artificial promotor candidate.

The methods for extracting a virtual amino acid sequence from a given nucleotide sequence and the methods for expressing the index curve, which index curve is based upon the virtual amino acid sequence, may be appropriately selected in order to make the changes at the transcription start site easier to observe.

In one example of a method for extracting a virtual amino acid sequence from a given nucleotide sequence, a virtual amino acid sequence can be generated from the nucleotide sequence by selecting each respective amino acid based upon units of three nucleotides and by moving along the nucleotide sequence one nucleotide at a time in order to select successive respective amino acids.

However, in addition to the above-mentioned method in which units of three nucleotides are extracted from the nucleotide sequence to select the amino acid and moving along the sequence one nuleotide at a time in order to generate virtual amino acid sequences, a variety of methods can be utilized. For instance, three connected and neighboring nucleotides could be extracted from a nucleotide sequence, three nucleotides could be extracted while omitting every other nucleotide, or three nucleotides could be extracted while omitting two nucleotides out of each three nucleotides.

Another artificial promotor candidate selection method of the present invention includes the following steps: a candidate nucleotide sequence for an artificial promotor is joined to the upstream end of a nucleotide sequence of a structural gene; units of three nucleotides are extracted from the nucleotide sequence of the artificial promotor present starting from the beginning of the nucleotide sequence then shifting down the nucleotide sequence one nucleotide per extraction; a first progression is obtained from the index values of the respective amino acids in the virtual amino acid sequence thereby formed; the first progression is smoothed to obtain a second progression; and the artificial promotor is selected as a potentially effective artificial promotor candidate if a sign change occurs near the transcription start site within the second progression.

In this artificial promotor candidate selection method, a nucleotide sequence is formed by joining the nucleotide sequence of a virtually designed artificial promotor upstream to the nucleotide sequence for a structural gene. Specifically, the nucleotide sequence of an artificial promotor is joined upstream of the nucleotide sequence for a structural gene that is targeted for transcription.

As was explained above, a large number of nucleotide sequences may be evaluated as potential artificial promoters. Therefore, the computation task is preferably performed using a computer. A computer can be used to perform the task of automatically generating nucleotide sequences of potentially effectively artificial promoters. Nucleotide sequences of artificial promotors, which are expected to have ascertain degree of effect according to the computer, may be then manually modified by a researcher. For example, artificial promotor nucleotide sequences are sometimes modified by changing a portion of a known artificial promotor nucleotide sequence.

Next, using a selected method, units of three nucleotides per extraction are extracted from the nucleotide sequence of the artificial promotor starting from the beginning of the nucleotide sequence in order to generate a virtual amino acid sequence. The index values of the respective amino acids from the virtual amino acid sequence are determined, and a first progression comprising the amino acid index values is generated.

Herein, the term "amino acid index value" (e.g., transfer free energy to lipophilic phase, von Heijne-Blomberg, 1979) refers to a numerical value that was determined based upon a variety of different measurements, presently 434 types of measurements, of the physical properties of amino acids, and which amino acid index values are available on the Internet. Amino acid index values are utilized herein, because certain higher information is present in the background, which information is not ascertainable simply by analyzing nucleotide sequences.

Next, the first progression is smoothed to produce a second progression. This smoothing may be accomplished, e.g., by summing and averaging a certain number (e.g., 3–6) of values following the value in question, summing and averaging a certain number (e.g., 3–6) of values preceding the value in question, or summing and averaging a certain number (e.g., 3–6) of sequential values before and after the value in question. In each of the above methods, although an average value is determined by dividing the sum of the added values by the number of values added, the sum of the values itself also could be used. The associated graph, as will be explained below in a plotting step, can realize an identical pattern by adjusting the scale of the graph. Smoothing is not required to be performed according to the above methods. Further, a variety of mathematical methods may be utilized to smooth the data. Smoothing may be performed, for example, according to a moving average. Any method is acceptable if smoothing is provided to an extent such that the pattern (variation) of a graph of a smoothed progression can be recognized.

Then, a determination is made as to whether or not the sign changes near the transcription start site in the second progression; if the sign does change, the artificial promotor is selected as a potentially effective artificial promotor candidate.

When the determination is made as to whether or not the sign changes near the transcription start site in the second progression, the progression and its corresponding values can be represented graphically in the form of an index curve, thereby simplifying the determination by highlighting the sign inversion (reversal) trends in the index curve near the transcription start site.

Using the above-mentioned artificial promotor candidate selection method of the present invention, artificial promotor candidates that are very likely to function as promoters are selected from a large number of virtually-created, artificial promoters; therefore, the number of promotors that must be actually tested in order to evaluate their effect can be reduced.

As shown in the lower half of FIG. 1, prior-art promoter design methods comprised the following steps: promoter candidates are synthesized to as to have random nucleotide sequences (S1), the promoter candidates are joined with a structural gene (gene for testing) (S2), the resulting product is introduced into a cell and the effectiveness of the promoter candidate is evaluated by checking for expression of the structural gene. According to the present invention, on the other hand, as illustrated in the top half of FIG. 1, promoter candidates are first selected in step S1 by using the above-described methods, the promoter candidates are then synthesized (S2) and joined with structural genes (genes for testing) (S3), and finally tested (S4). Thus, the number of promotors that must be actually synthesized and tested is reduced.

BRIEF EXPLANATION OF THE DRAWINGS

FIG. 1 illustrates the effect of the present invention.

FIG. 3 illustrates methods for converting from a nucleotide sequence (containing SEQ ID NOs: 6 and 7) to an amino acid index sequence. The pattern 1, 2 and 3 nucleotide sequences include nucleotides 1 to 17 of SEQ ID NO: 2.

FIG. 4 is a genetic code table.

FIG. 5 shows representative amino acid index values.

FIG. 6 is a conceptual illustration of an index curve.

FIG. 7 shows the nucleotide sequence of the promotor region of Gene J01567 (SEQ ID NO: 1).

FIG. 8 shows the nucleotide sequence of the promotor region of Gene X87994 (SEQ ID NO: 2).

FIG. 9 shows the nucleotide sequence of the promotor region of Gene EPD31005 (SEQ ID NO: 3).

FIG. 10 shows the nucleotide sequence of the promotor region of Gene EPD35038 (SEQ ID NO: 4).

FIG. 11 shows the nucleotide sequence of the promotor region of Gene J01567 (SEQ ID NO: 1) in order of one nucleotide at a time beginning from the upstream.

FIG. 12 shows a sequence created by extracting nucleotides from the nucleotide sequence shown in FIG. 11 in groups of three (SEQ ID NO: 5).

FIG. 13 shows a progression obtained by converting the sequences of three nucleotides shown in FIG. 12 into amino acid index values.

FIG. 14 shows a progression obtained by smoothing the progression shown in FIG. 13.

PREFERRED EMBODIMENTS OF THE INVENTION

Figure 2:
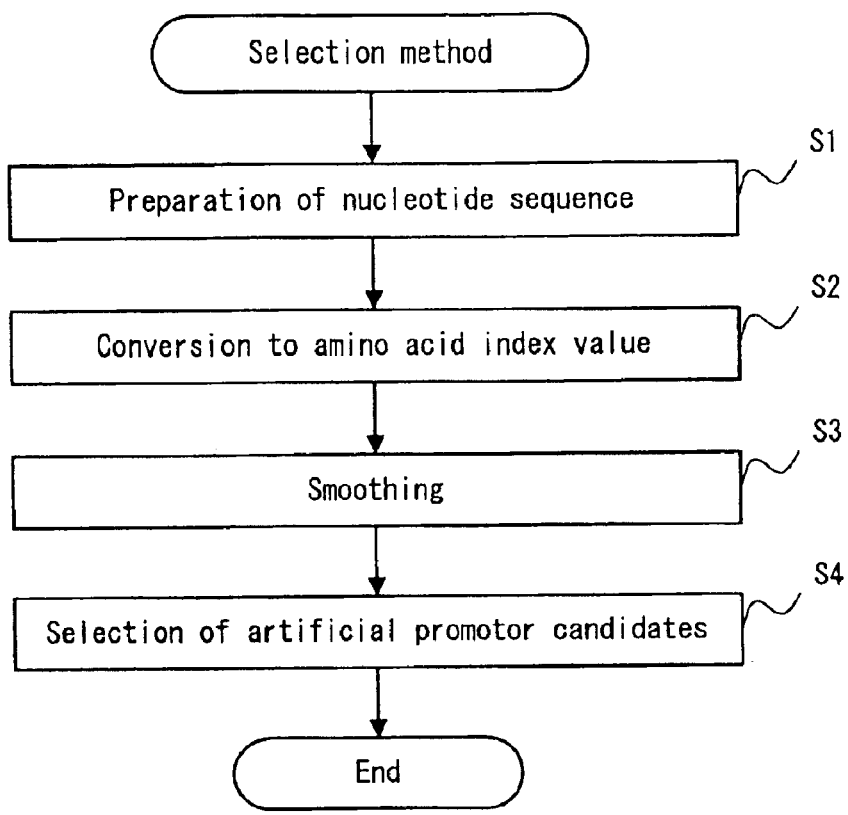
FIG. 2 is a flowchart illustrating a method for selecting artificial promotor candidates of the present invention.

Hereinafter, embodiments of the artificial promotor candidate selection methods of the present invention will be discussed FIG. 2 shows a method for selecting artificial promotor candidates.

As shown in FIG. 2, in the artificial promotor candidate selection methods of the invention, a virtual nucleotide sequence is created by joining the nucleotide sequence of a virtual artificial promotor to the nucleotide sequence of a structural gene (gene for testing) (S1).

This step will be described in greater detail using FIG. 3. As shown in FIG. 3, the nucleotides of the virtually created artificial promotor nucleotide sequence are gatct . . . ca, and the nucleotides of the structural gene are cccgtccag . . . . In Step S1, the gatct . . . ca sequence of the artificial promotor nucleotide sequence is inserted before the cccgtccag . . . nucleotide sequence of the structural gene, thereby generating the nucleotide sequence gatct . . . cacccgtccag . . . . (containing SEQ ID NOs: 8 and 7).

Next, a first progression is prepared, which first progression includes the amino acid index values of the virtual amino acid index sequence. The virtual amino acid index sequence is generated by extracting nucleotides in units of three in a pre-determined pattern starting from the first nucleotide in the sequence (S2).

An example of a method for sequentially extracting nucleotides in units of three from the nucleotide sequence will be presented. Pattern 1 is a method for sequentially extracting nucleotides in units of three starting at the beginning of the nucleotide sequence gatct . . . and shifting one nucleotide per extraction. The first three nucleotides extracted by this method are gat, the second three nucleotides are atc, and the third three nucleotides are tct.

As shown in FIG. 4 (genetic code table), the three nucleotides gat correspond to aspartic acid (D: hereinafter, amino acids will be referred to by their single-letter codes), atc corresponds to isoleucine (I), and tct corresponds to serine (S). Therefore, the amino acid sequence produced by extracting nucleotides in units of three, while shifting one nucleotide per extraction, from this nucleotide sequence is represented by the virtual amino acid sequence D, I, S, L, S . . . . (SEQ ID NO: 9).

Once the virtual amino acid sequence is prepared, the respective amino acids within the virtual amino acid sequence are converted into their respective index values to create a progression. von Heijne-Blomberg's transfer free energy to lipophilic phase is presented in FIG. 5 as an example of amino acid index values for the 20 types of amino acids. Thus, the above amino acid sequence is converted into the following progression of numerical values (Progression 1): 23.22, −18.32, −1.54, −17.79, −1.54 . . . , which corresponds to the first progression as utilized in the claims.

If a stop codon (X) is encountered in the amino acid sequence, then there is no corresponding amino acid or amino acid index value, thus, in this embodiment, the amino acid index value of the stop codon (X) is zero. Removal of the stop codon (X) would result in the removal of a nucleotide from the nucleotide sequence, which would change the amino acid index curve.

Next, Progression 1 (23.22, −18.32, −1.54, −17.79, −1.54 . . . ) is smoothed (S3). Progression 1 is smoothed in this step because changes (patterning) in the amino acid index values in Progression 1 are difficult to recognize due to extreme variation in neighboring values. Therefore, smoothing may be performed so that a graph containing the smoothed numbers will have a discernable pattern.

Any of several known smoothing methods in the field of data processing may be used, but as an example for the purpose of explanation, the values of Progression 1 will be smoothed by taking the average of a certain number (3) of these values and sequentially moving toward the end of the virtual sequence in order to generate a smoothed progression.

The average of the first three values of Progression 1 (23.22, −18.32, −1.54, −17.79, 348 −1.54 . . . ) is (23.22+(−18.32)+(−1.54))/3=1.12, the average of the next three values is (−18.32)+(−1.54)+(−17.79))/3=−12.55, and the average of the next three values is (−1.54+(−17.79)+(−1.54))/3=−6.96. The averages of the subsequent values are generated in a similar manner.

Taking the average for Progression 1 for every few values results in a smoothed Progression 2 (1.12, −12.55, −6.96 . . . ), which corresponds to the second progression as used in the claims.

Next, a determination is made as to whether or not there is a sign inversion in Progression 2 near the transcription start site; if there is a sign inversion, the artificial promotor is selected as a potentially effective artificial promotor candidate.

This determination method preferably produces an index curve by graphing Progression 2 and evaluates the particular artificial promotor based on the pattern of the index curve. (S4).

The positions of the numerical values of Progression 2 (1.12, −12.55, −6.96 . . . ) are plotted onto the horizontal axis, and th smoothed amino acid index values are plotted onto the vertical axis in order to create an index curve. FIG. 6 conceptually illustrates an example of a portion of an index curve around the transcription start site.

Artificial promotor candidates that are very likely to function as promoters can be selected based upon the pattern of the index curve of a virtual amino acid sequence around the transcription start site.

As discussed above, index curves of known promotors typically show a sign reversal (observable in FIG. 15) near the transcription start site. If the index curve of the virtual amino acid sequence, which is prepared by joining a virtual artificial promotor nucleotide sequence to a nucleotide sequence of a structural gene, exhibits a sign reversal near the transcription start site, the virtual artificial promotor having this nucleotide sequence could be selected as an artificial promotor candidate as possibly being effective for the structural gene.

The efficacy of this artificial promotor candidate selection method will be described below in terms of genes (promotor regions) having known nuclcotide sequences.

The selected genes (promotor regions) having known nucleotide sequences were J01567 Plasmid Colicin E1 (from *E. coli*) strong promotor region DNA, X87994 *C. xyli* DNA for strong promotor (569 bp), EPD31005 (+)Ph EPSP synthase P2+, and EPD35038 (+)Le LAT52; range −499 to 100.

The nucleotide sequences of J01576 and X87994 were obtained from the DNA Data Bank of Japan (DDBJ), and the other sequences were found in the Eukaryotic Promotor Database (EPD). (X87994 sequence data was used beginning at number 481.)

These nucleotide sequences are shown in FIGS. 7 to 10. The nucleotide sequence of J01567 is shown in FIG. 7, and the transcription start site is found at number 84. The nucleotide sequence of X87994 is shown in FIG. 8 and the transcription start site is found at number 542. (Note that this transcription start site corresponds to number 62 in FIG. 15(*b*), because the sequence listing in FIG. 15 begins with number 481.) The nucleotide sequence of EPD31005 is shown in FIG. 9 and the transcription start site is found at number 140. Finally, the nucleotide sequence of EPD35038 is shown in FIG. 10 and the transcription start site is found at number 140.

The index curve of the nucleotide sequence was plotted according to the methods described above, which will be described in detail with reference to FIGS. 11 to 14, and using as an example J01567, which nucleotide sequence is shown in FIG. 7. The index curve generating method, which is described below, is only one example and does not limit the present invention.

(1) Three sequential nuclcotides are repeatedly extracted as units starting from the beginning of nucleotide sequence J01567, which is shown in FIG. 11, by moving one nucleotide per extraction until the final nucleotide is reached, thereby generating the sequence shown in FIG. 12, which lists the nucleotides in groups of three.

(2) The three nucleotide units are then converted into the corresponding amino acids using the sequence generated in the above Step (1))(FIG. 12), thereby generating a virtual amino acid sequence.

(3) The progression shown in FIG. 13 is then calculated, which progression includes amino acid index values obtained by converting each amino acid within the sequence generated in the above Step (2) into the corresponding hydrophobic amino acid index value.

(4) The progression shown in FIG. 14 is then calculated, which progression contains values generated by adding the five values in front of each value from the progression generated in the above Step (3) (FIG. 13).

(5) An index curve is produced by graphing the progression generated in the above Step (4) (FIG. 14) along the horizontal axis starting from the first nucleotide and by expressing the amino acid index value corresponding to each position on the vertical axis.

Figure 15:
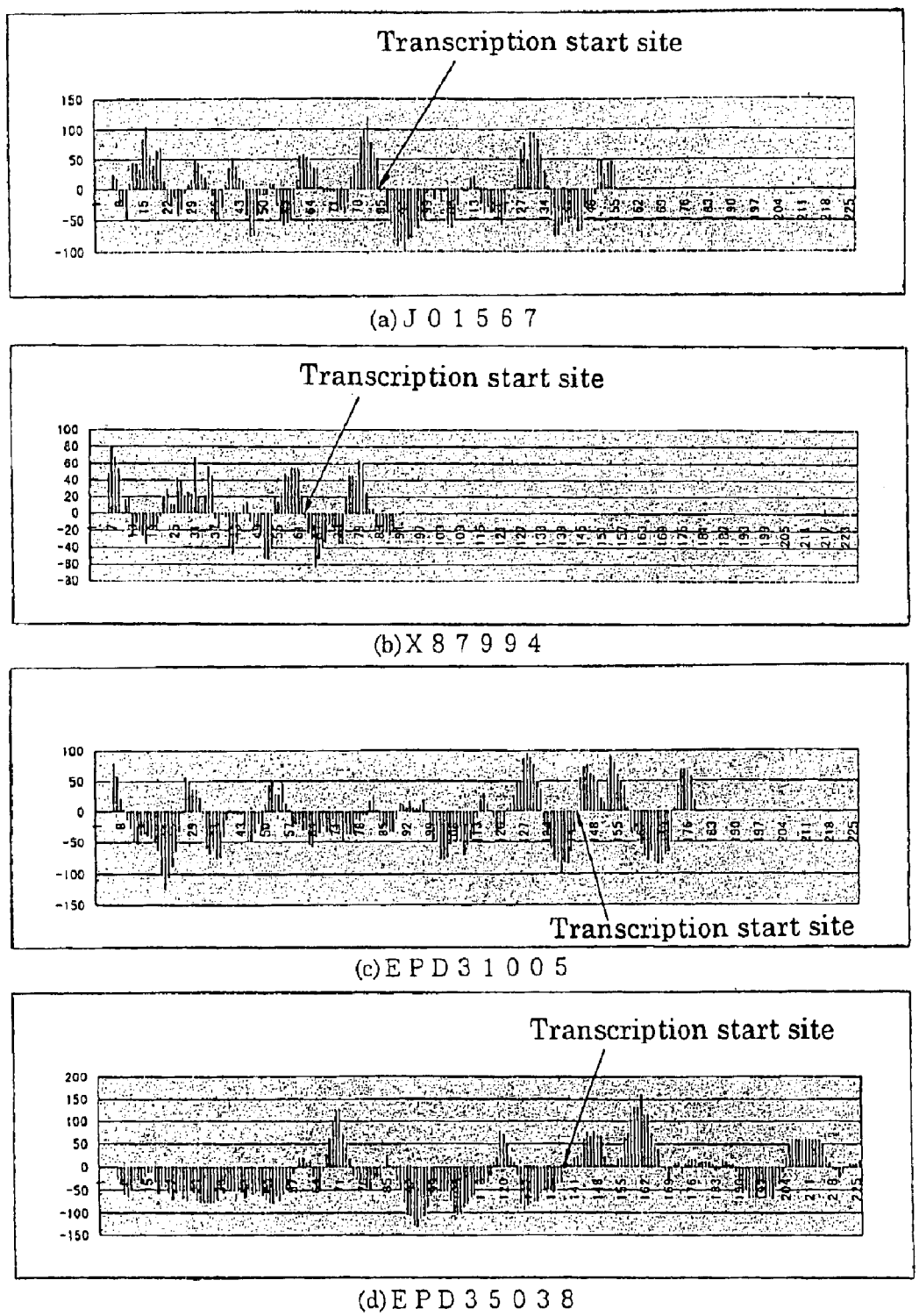
FIG. 15 shows representative index curves generated from known promoters.

The resulting index curves are shown in FIG. 15. (The graphs are expressed in a bar-graph format in order to visually enhance the sign reversals.)

Index curves produced from the nucleotide sequences of the above identified four genes are shown in FIG. 15. Each index curve exhibits a sign reversal near the transcription start site.

By creating index curves of virtual amino acid sequences, which are obtained by joining the nucleotide sequence of a virtual artificial promotor to a nucleotide sequence of a structural gene, virtual artificial promotors can be selected as potentially effective artificial promotor candidates for the structural gene in question when a sign change is present in the index curve near the transcription start site. The artificial promotor candidates thus selected are subsequently synthesized, joined to the actual corresponding nucleotide sequence, and tested in order to make a final evaluation.

When artificial promotor candidates are selected according to the above method, the number of artificial promotor candidates actually synthesized and tested can be dramatically reduced, and potentially effective artificial promotor candidates (i.e., nucleotide sequences) can be efficiently designed.

When the nucleotide sequence of a potentially effective artificial promotor is being designed, the portion of the index curve that is evaluated can be limited to the portion near the transcription start site in order to simplify the evaluation.

If artificial promotor candidates having high transcription activity can be effectively designed using the methods of the present invention, then promotors useful in the field of gene therapy, for example, could be efficiently designed. Cancer cells, for example, could be infected with an adequate amount of a virus (a normal gene-carrying vector virus) in order to cause specific expression of proteins from these normal genes (integrated with powerful artificial promotors) in amounts that are adequate to suppress the cancer. An artificially strong active promotor must be designed in order to cause specific and powerful expression of the normal gene.

Figure 16:
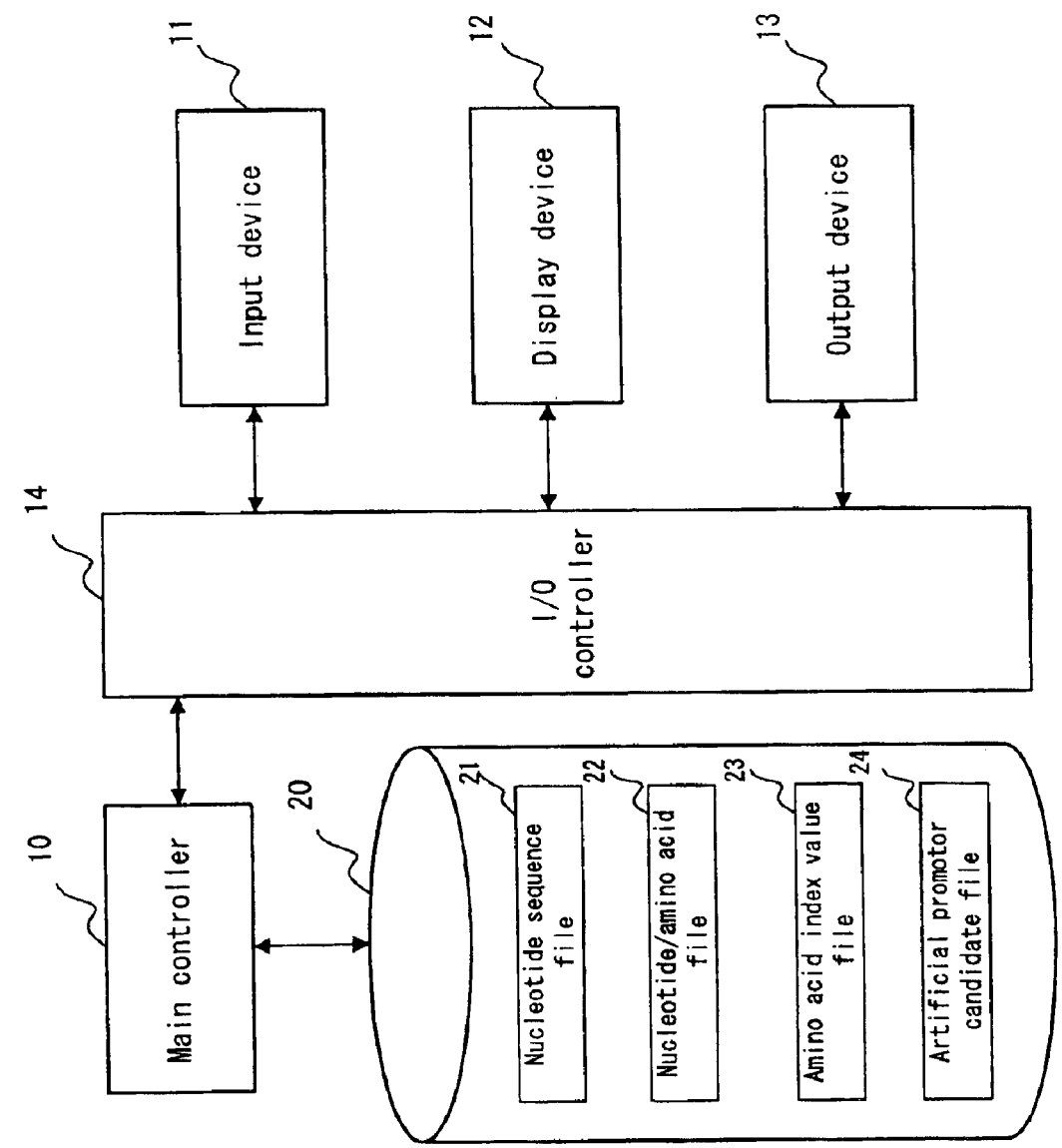
FIG. 16 is a hardware configuration diagram showing the artificial promotor candidate selection device of one embodiment of the present invention.

An embodiment of an artificial promotor candidate selection device of the present invention, which is capable of selecting favorable artificial promotor candidates, will be described. FIG. 16 is a hardware configuration diagram of the artificial promotor candidate selection device of this embodiment.

As shown in FIG. 16, the artificial promotor candidate selection device of this embodiment includes a controller 10 (hereinafter referred to as a main controller), which is programmed to control the entire artificial promotor candidate selection device, a memory device 20 connected to the main controller 10 that stores various types of data, an input device 11 comprising a keyboard, mouse, or other pointing device connected to the main controller 10 via a I/O controller 14, a display device 12, such as a monitor that shows index curves and other images, and an output device 13, such as a printer, that prints the nucleotide sequences of selected promotor candidates. The main controller 10 includes an operating system (OS) or other control program, a conversion program for generating a first progression, in which an input nucleotide sequence is converted to amino acid index values, a program for smoothing the first progression, an image processing program for displaying the smoothed data on the display device 12, and an internal memory for storing required data.

The memory device 20 is a storage means, such as a hard disk, floppy disk, or optical disk, and stores a nucleotide sequence file 21, a nucleotide/amino acid file 22, an amino acid index value file 23, and an artificial promotor candidate file 24 that contains the nucleotide sequences of selected artificial promotor candidates.

The nucleotide sequence file 21 is a file containing nucleotide sequences created by joining the nucleotide sequence of a virtually produced artificial promotor candidate to the nucleotide sequence of a structural gene. Nucleotide sequences input by the operator via the keyboard or other implement of input device 11 are stored in the memory device 22.

The nucleotide/amino acid file 22 is a file containing data that converts the various three-nucleotide combinations into the corresponding amino acids. Specifically, it contains data such as the data shown in FIG. 4.

The amino acid index value file 23 is a file containing the amino acid index values of alanine, arginine, and the other amino acids. Specifically, the amino acid index value file 23 comprises data such as the data shown in FIG. 5.

The artificial promotor candidate file 24 is a file containing artificial promotor nucleotide sequences selected as being highly likely to effectively function as artificial promotors based upon the determination using the generated index curve.

Figure 17:
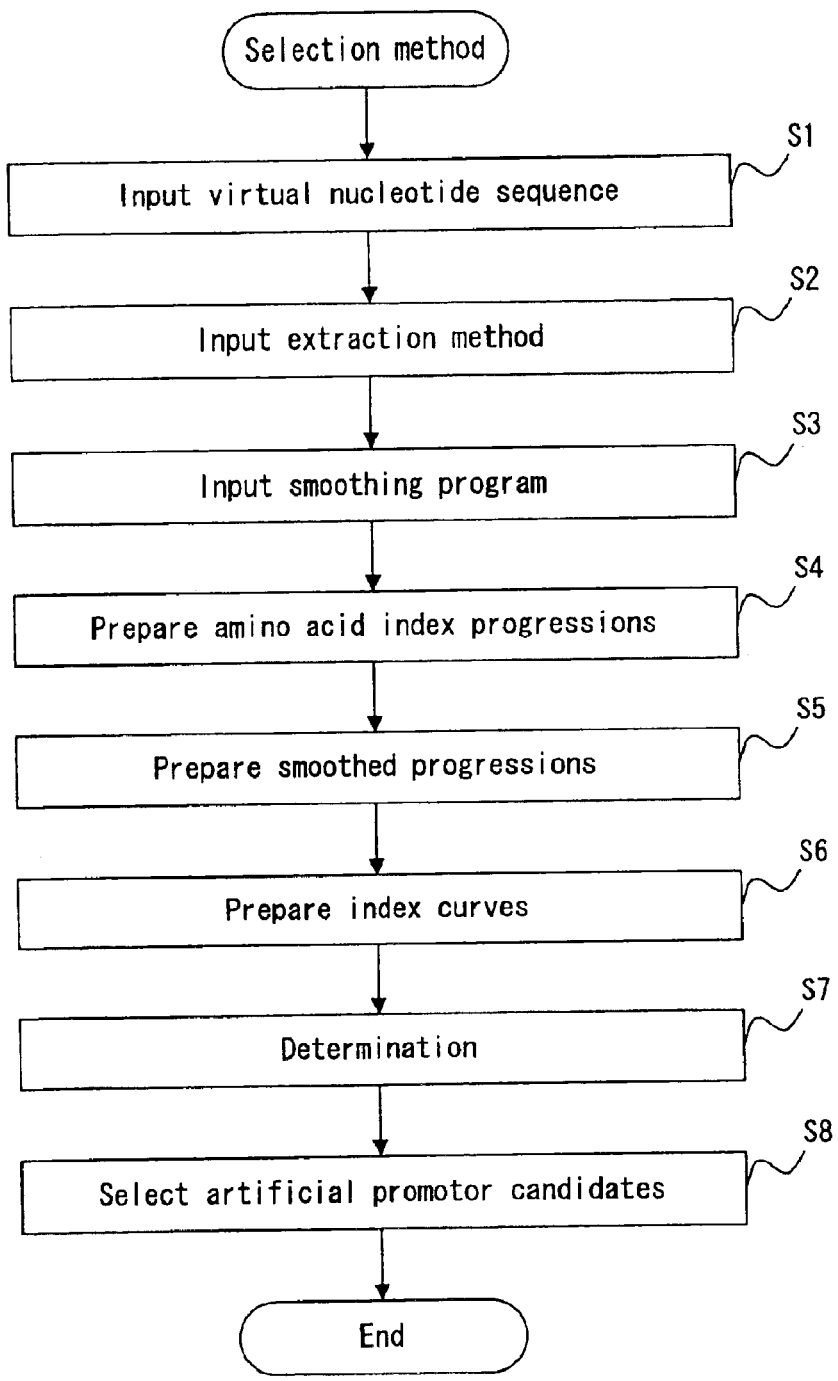
FIG. 17 is a flowchart illustrating a method for selecting artificial promotor candidates using the artificial promotor candidate selection device shown in FIG. 16.
Figure 18:
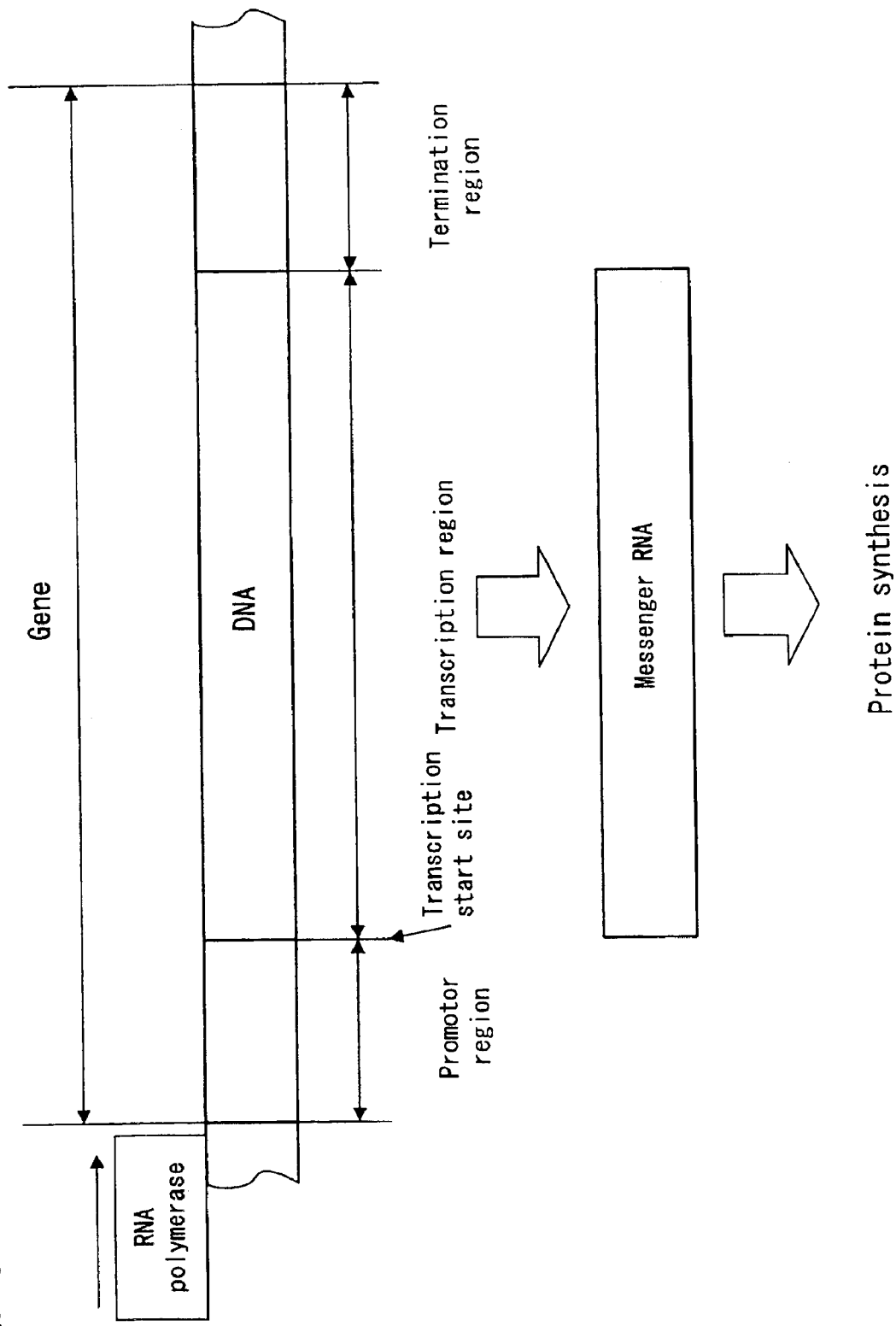
FIG. 18 illustrates the steps of DNA transcription and protein synthesis.

Next, a method for selecting artificial promotor candidates from nucleotide sequences input using the artificial promotor candidate selection device of this embodiment will be described with reference to FIG. 17, which is a flowchart illustrates the method for selecting artificial promotor candidates.

First, an operator inputs a virtual nucleotide sequence via the input device 11, which virtual nucleotide sequence includes the nucleotide sequence of a virtual promotor joined to the nucleotide sequence of a structural gene (S1). The nucleotides input by the operator are displayed as e.g., a, g, c, or t, on the display device 12 so the operator can perform data entry while monitoring the input. The nucleotide sequence is stored in the nucleotide sequence file 21 of the memory device 20 via the I/O controller 14 and the main controller 10. This example will concern inputting one nucleotide sequence (artificial promotor candidate).

Next, via the input device 11, the operator inputs steps for extracting units of three nucleotides from the nucleotide sequence input in Step S1 (S2). As shown in FIG. 3, the promotor candidate selection device of this embodiment can utilize Selection Method 1, in which three sequential nucleotides are extracted, Selection Method 2, in which three nucleotides are extracted by omitting every other one nucleotide, or Selection Method 3, in which three nucleotides are extracted by selecting one nucleotide out of each three nucleotides (See FIG. 3).

The operator additionally inputs a smoothing program via the input device 11 (S3). In the artificial promotor candidate selection device of this embodiment, a plurality of values (3 to 10) is input to determine the average.

Once the data is input in Steps S1 to S3, the main controller 10 extracts three nucleotides from the nucleotide sequence input in Step S1 according to the extraction method input in Step S2. The virtual amino acid sequence formed by this nucleotide sequence is converted into amino acid index values, thereby generating a first progression (S4). That is, groups of three nucleotides are extracted from the nuclcotide sequence stored in the nucleotide sequence file 21, the amino acids corresponding to the nucleotide sequence are selected based upon the data stored in the nucleotide/amino acid file 22 and subsequently, the amino acids are converted into the first progression based upon the data stored in the amino acid index value file 22. The first progression thus created is stored in an internal memory within the main controller 10.

Next, the main controller 10 smoothes the first progression stored in the internal memory (S5). Then, the main controller 10 displays an index curve on the display device 12 based upon the smoothed values (S6). In this embodiment, smoothing is performed by taking the average of a number of values, which number corresponds to the number input in Step S3 (e.g., 3). A detailed explanation of this smoothing method was provided above.

Then, based upon the index curve displayed on the display device 12, the operator determines the efficacy of the candidate promotor having the virtual nucleotide sequence (S7). Specifically, the index curve for the input nucleotide sequence is displayed on the display device 12, the operator observes the index curve and the operator determines whether or not a sign change exists near the transcription start site.

When a promotor is determined to have a high likelihood of functioning as an artificial promotor in Step S7, the corresponding nucleotide sequence is selected as an artificial promotor candidate (S8). The nucleotide sequence of the selected artificial promotor candidate is stored in the artificial promotor candidate file 24 within the memory device 20, and the operator can display it on the display device 12 or output it using an output device (printer) on an as-needed basis.

As described above, in the artificial promoter candidate selection device of this embodiment, the simple input by an operator of a nucleotide sequence, which is the nucleotide sequence of a virtual artificial promoter candidate and the nucleotide sequence of a targeted structural gene, allows a determination to be made as to whether or not the virtual promoter candidate could potentially function as an artificial promoter, thereby reducing the number of artificial promoter candidates required to be actually synthesized and tested to a certain extent and enabling efficient artificial promoter design.

Although the description of this embodiment concerned an example in which only one nucleotide sequence (artificial promoter candidate) was input, a plurality of nucleotide sequences can be input at one time and stored in the nucleotide sequence file 21 of the memory device 20. In such case, Steps S2 to S8, shown in FIG. 17, would be repeated for each nucleotide sequence stored in the nucleotide sequence file 21.

The operator is not required to input nucleotide sequences as discussed above. Instead, the items input into the artificial promoter candidate selection device could be limited to the number of nucleotides for the artificial promoter and the nucleotide sequence of the structural gene. The main controller 10 would then automatically generate all conceivable nucleotide sequences.

That is, DNA comprises four nucleotides a, g, c, and t. Therefore, if the number of nucleotides in the promoter region (n) is known, then all conceivable nucleotide sequences ($4^D$) could be automatically created and combined with the nucleotide sequence of a structural gene. By equipping the artificial promoter candidate selection device with such an automatic nucleotide sequence generating means, artificial promoter candidates could be efficiently generated and the determination of the efficacy thereof could be efficiently performed; thus, nucleotide sequence analysis could be performed without the omissions associated with prior art random artificial promoter generation.

In the above description, an operator (researcher) evaluates the index curves displayed on the display device 12; however, computer pattern recognition technology could be employed to enable automatic recognition by the main controller 10. The device also could be combined with a means for automatically generating nucleotide sequences that automatically generates nucleotide sequences using the main controller 10 and automatically evaluates the index curves using the main controller 10, thereby enabling automatic evaluation of all nucleotide sequences.

Although the preferred embodiments of the present invention have been described above, each is but an example, and the invention may be embodied through a variety of modifications or improvements based on the knowledge of persons skilled in the art.

What is claimed is:

1. A method for selecting an artificial promoter candidate, comprising:

generating a first virtual amino acid sequence from a candidate nucleotide sequence and generating an amino acid index curve from the first virtual amino acid sequence, generating a second virtual amino acid sequence from a nucleotide sequence near a transcription start site of a transcription region of a gene and generating an amino acid index curve from the second virtual amino acid sequence, and selecting the candidate nucleotide sequence as an artificial promotor candidate if the amino acid index curve of the candidate nucleotide sequence has a sign opposite of the amino acid index curve of the nucleotide sequence near the transcription start site of the transcription region.

2. A method for selecting an artificial promotor candidate, comprising the steps of:

joining nucleotide sequence data of an artificial promotor to an upstream side of nucleotide sequence data of a transcription region of a gene; and selecting the artificial promotor as a promotor candidate for the transcription region when an amino acid index curve based on a virtual amino acid sequence, which is obtained from the joined nucleotide sequence data, exhibits a sign change near the transcription start site of the transcription region.

3. A method as claimed in claim 2, wherein the virtual amino acid sequence, which is obtained from the joined nucleotide sequence data, is generated based on amino acid units formed from units of three nucleotides each extracted from the joined nucleotide sequence data while shifting one nucleotide for each extraction.

4. A method for selecting a potentially effective artificial promotor candidate, comprising the steps of:

generating joined nucleotide sequence data by joining nucleotide sequence data representing a candidate artificial promotor to an upstream side of nucleotide sequence data representing a transcription region of a gene;

generating a first progression from index values of respective amino acids found in a virtual amino acid sequence formed from units of three nucleotides each extracted from the joined nucleotide sequence data starting at the beginning of the joined nucleotide sequence data and shifting one nucleotide for each extraction;

smoothing the first progression, thereby obtaining a second progression; and selecting the candidate artificial promotor as a potentially effective artificial promotor candidate if the sign of the second progression changes near position of the transcription start site of the transcription region.

5. An artificial promotor candidate selection device comprising:

means for generating an amino acid index curve based upon index values of respective amino acids in a virtual amino acid sequence, which is obtained from nucleotide sequence data generated by joining nucleotide sequence data of an artificial promotor to an upstream side of nucleotide sequence data of a transcription region of a gene; and means for selecting the artificial promotor as a promotor candidate for the transcription region when the sign of the amino acid index curve changes near the transcription start site of the transcription region.

6. An artificial promotor candidate selection device comprising:

means for generating joined nucleotide sequence data by joining nucleotide sequence data of a candidate artificial promotor to an upstream side of nucleotide sequence data of a transcription region of a gene;

means for generating a first progression from index values of respective amino acids in a virtual amino acid sequence formed from units of three nucleotides each extracted from the joined nucleotide sequence data starting at the beginning of the joined nucleotide sequence data, which is generated by the joined nucleotide sequence data generating means, and shifting one nucleotide for each extraction;

means for generating a second progression by smoothing the first progression, which is generated by the first progression generating means; and means for selecting the candidate artificial promotor as a potentially effective artificial promotor if the sign of the second progression, which is obtained by the second progression generating means, changes near the transcription start site of the transcription region.

7. A computer-readable storage medium storing a program for selecting an artificial promotor as a promotor candidate for a transcription region of a gene by joining nucleotide sequence data of the artificial promotor upstream of nucleotide sequence data of the transcription region when an amino acid index curve based on a virtual amino acid sequence, which is obtained from the joined nucleotide sequence data, exhibits a sign change near the transcription start site of the transcription region.

8. A computer-readable storage medium storing a program comprising the steps of: generating joined nucleotide sequence data by joining nucleotide sequence data of a candidate artificial promotor to an upstream side of nucleotide sequence data of a transcription region of a gene in order to identify potentially effective artificial promotor candidates for the transcription region;

generating a first progression from index values of respective amino acids in a virtual amino acid sequence formed from units of three nucleotides each extracted from the joined nucleotide sequence data starting at the beginning of the joined nucleotide sequence data and shifting one nucleotide for each extraction;

smoothing the first progression, thereby generating a second progression; and selecting the candidate artificial promotor as a potentially effective artificial promotor if the sign of the second progression changes near the transcription start site of the transcription region.

* * * * *